United States Patent [19]

Okamura et al.

[11] Patent Number: 4,746,617
[45] Date of Patent: May 24, 1988

[54] METHOD OF ANALYZING NITROGEN CONTAINED IN TITANIUM GROUP METAL OR ALLOY THEREOF

[75] Inventors: Masayoshi Okamura, Kobe; Kiyoshi Matsuda, Takasago; Hiromichi Yamada, Akashi; Hiromi Umeda; Masami Tomimoto, both of Himeji, all of Japan

[73] Assignee: Kabushiki Kaisha Kobe Seiko Sho, Kobe, Japan

[21] Appl. No.: 3,614

[22] Filed: Jan. 15, 1987

Related U.S. Application Data

[62] Division of Ser. No. 739,271, May 30, 1985, Pat. No. 4,673,655.

[51] Int. Cl.$^4$ ............ G01N 33/20; C01G 23/00; C22C 14/00
[52] U.S. Cl. ............................ 436/75; 436/83; 436/84; 436/159; 436/160; 423/598; 423/608; 420/417
[58] Field of Search ............ 436/75, 83, 84, 115, 436/159; 423/608, 598; 420/417; 75/84

[56] References Cited

U.S. PATENT DOCUMENTS 4,456,580 6/1984 Yamada et al. ............... 436/115 X
4,525,328 6/1985 Bredeweg ..................... 436/159 X

FOREIGN PATENT DOCUMENTS 2458807 2/1981 France ............................ 436/159

Primary Examiner—Barry S. Richman
Assistant Examiner—Lynn M. Kummert
Attorney, Agent, or Firm—Oblon, Fisher, Spivak, McClelland & Maier

[57] ABSTRACT

A method of quantitatively analyzing nitrogen contained in titanium group metal or an alloy thereof, involving melting the metal or alloy in an inert gas atmosphere, allowing the nitrogen in titanium to be extracted and subjecting the extracted nitrogen to a quantitative analysis, characterized in that a titanium sample for analysis is melted in the present of nickel in an amount corresponding to 7 to 16 times the weight of the sample.

7 Claims, 4 Drawing Sheets

WEIGHT RATIO OF NICKEL OR PLATINUM TO SAMPLE

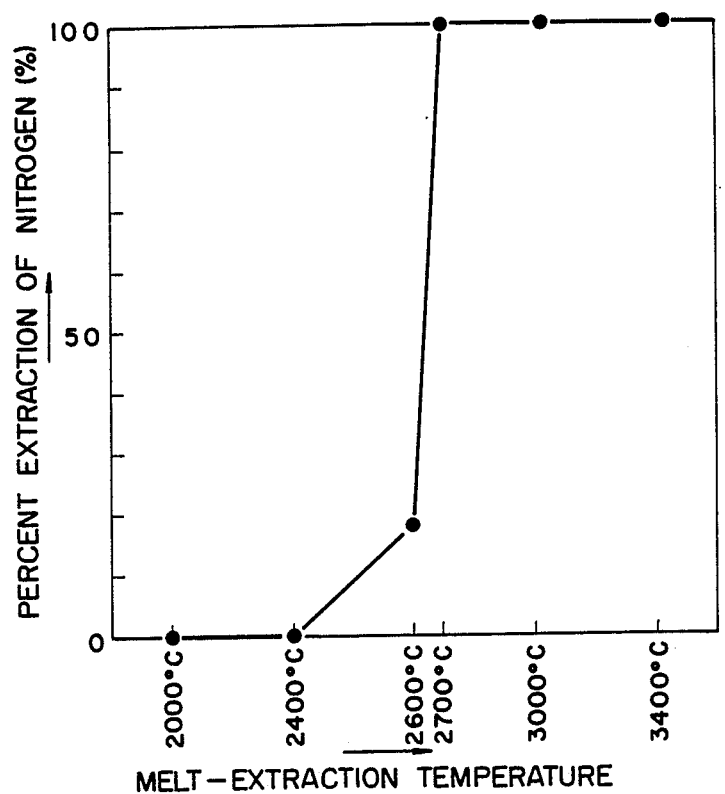

METHOD OF ANALYZING NITROGEN CONTAINED IN TITANIUM GROUP METAL OR ALLOY THEREOF

This application is a division of copending prior application Ser. No. 739,271, filed on May 30, 1985, now U.S. Pat. No. 4,673,655.

BACKGROUND OF THE INVENTION

1. Field of the Invention

The present invention relates to a method of analyzing oxygen or nitrogen contained in a titanium group metal or an alloy thereof. More particularly, it is concerned with a method of quantitatively determining oxygen contained in such metal or alloy by melting the metal or alloy at a high temperature in an inert gas atmosphere to react the oxygen with carbon, extracting it as carbon monoxide and analyzing the latter. It is also concerned with a method of quantitatively determining nitrogen contained in such metal or alloy by melting the metal or alloy at a high temperature in an inert gas atmosphere to thereby extract the nitrogen and analyze it.

2. Description of the Prior Art

It is well known that oxygen contained as a valuable element in for example titanium, like nitrogen contained therein, is occluded between the crystal lattices of titanium and exerts a great influence on strength and other mechanical properties. And the content of such oxygen or nitrogen is specified also in the Material Standards. Therefore, advancement of the technique for adjusting and controlling the content of oxygen or nitrogen obtained in titanium is desired, and at the same time, also as to the technique for analyzing such oxygen or nitrogen, it is necessary to make a thorough study.

Heretofore, as the method of analyzing oxygen contained in titanium, there has generally been adopted a method in which a sample for analysis (hereinafter referred to simply as "sample") is placed in a crucible made of graphite, then heat-melted at a high temperature in an inert gas atmosphere such as helium to allow reaction to proceed as shown by the following formula (1) and the resulting carbon monoxide is extracted and then determined quantitatively according to an infrared absorption method or a thermal conductivity method.

$$\underline{C} + \underline{O} = CO(g) \qquad (1)$$

For analysis of nitrogen contained in titanium, there has generally been adopted a method in which a sample is placed in a graphite crucible, then heat-melted at a high temperature in an inert gas atmosphere such as helium to allow reaction to take place as shown by the following formula (2) and the resulting nitrogen gas (N₂) is extracted and determined quantitatively according to a thermal conductivity method.

$$2\underline{N} = N_2(g) \qquad (2)$$

In the above formulae, the element symbols underlined indicate that the underlined elements are occluded in molten titanium.

Titanium has a strong affinity for oxygen and nitrogen, so it is difficult to extract oxygen or nitrogen contained in titanium completely as carbon monoxide or nitrogen gas. Further, since titanium has a good wettability for a graphite crucible, it permeates into graphite upon melting with the result that only 1% or less of the actual content can be extracted.

In order to solve the above-mentioned problem, there has been proposed and practised a method (platinum bath method) in which platinum is melted together with a titanium sample. The platinum bath method is at present recommended and adopted widely because of superior analytical accuracy and reproducibility for the following reasons: (1) the solubility of oxygen or nitrogen in molten platinum is small and so the foregoing reaction is accelerated in extraction, (2) since the melting point of titanium and that of platinum is about the same (titanium: 1670° C., platinum: 1773° C.), the bath formation is easy, and (3) the solubility of carbon in molten platinum is also small and so the graphite crucible is not eroded. However, the platinum bath method is uneconomical because platinum is very expensive.

SUMMARY OF THE INVENTION

Having made extensive studies for establishing a new analyzing method for oxygen or nitrogen contained in titanium, free of the above-mentioned drawbacks and capable of according accuracy and reproducibility equal to those in the platinum bath method, the present inventors found that even when nickel was used under specific conditions in place of platinum, there could be obtained accuracy and reproducibility which were by no means inferior to those in the platinum bath method. Thus, the present invention was accomplished.

More specifically, the present invention resides in a method involving melting titanium in an inert gas atmosphere in a graphite crucible to allow oxygen contained therein to react with carbon monoxide and extract, or nitrogen contained therein to extract, and subjecting it to a quantitative analysis, characterized in that a titanium sample is melted in the presence of nickel in an amount corresponding to 7 to 17 (7 to 16 for nitrogen analysis) times the weight of the sample.

BRIEF DESCRIPTION OF THE DRAWINGS

FIG. 5 shows a relation between melt-extraction temperature and percent extraction of nitrogen.

DESCRIPTION OF PREFERRED EMBODIMENTS

Figure 1A:
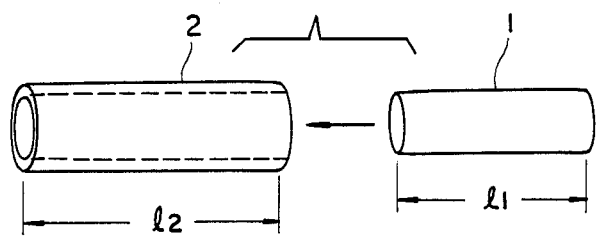
FIG. 1 schematically illustrates the form of titanium sample and nickel used in the present invention.

The present invention will be described in detail hereinunder mainly about the results of experiments.

The method of melting a titanium sample in the presence of nickel is advantageous in that nickel per se, like the foregoing platinum, is small in solubility to oxygen and nitrogen and is very effective in extracting oxygen as carbon monoxide or nitrogen as nitrogen gas, and the crucible used is little eroded. However, there exists the problem that the melting point (1,455° C.) of nickel is lower by about 200° C. than the melting point (1,670° C.) of titanium and so with a conventional method it is difficult to melt both simultaneously. The present inventors thought it is difficult to melt both simultaneously. The present inventors thought it impossible to put the nickel bath method to practical use unless this problem was overcome, and repeated various experiments in order to solve the problem. As a result, we found that the form of nickel added and the nickel to sample ratio were very important factors to attain desired analytical accuracy and reproducibility.

More particularly, as to the form of nickel, we tried to put a high purity nickel (purity: not lower than 99% by weight) into a graphite crucible in three forms of powder, wire and plate simultaneously with a sample.

Table 1 shows the results of experiments in which powder (20 mesh), wire (1 mm dia. with sample wound thereon) and plate (0.4 mm thick with sample wrapped therein) of nickel were each placed in a graphite crucible together with about 0.1 g. of a standard sample (oxygen 0.187%) whose oxygen content had been determined beforehand by the platinum bath method, in an amount corresponding to ten times the weight of the sample and heat-melted at 2,700°–3,000° C., the resultant carbon monoxide was extracted and oxygen contained in the sample was quantitatively determined according to an infrared absorption method. Results obtained in the absence of nickel are also shown in the same table.

Table 2 shows the results of measuring the time required for completing the extraction of carbon monoxide produced in melt-extraction.

TABLE 1

Results of oxygen analysis in various shapes of nickel
(Extraction temperature: 2,700–3,000° C.)

| Number of times of analysis | Nickel Component | | | |
|---|---|---|---|---|
| | Not Added O | Powder (20 mesh) O | Wire O | Plate O |
| 1 | 0.0003 | 0.167 | 0.179 | 0.186 |
| 2 | 0.0002 | 0.120 | 0.188 | 0.188 |
| 3 | 0.0006 | 0.089 | 0.168 | 0.191 |
| 4 | 0.0003 | 0.142 | 0 191 | 0.187 |
| 5 | 0.0008 | 0.114 | 0.154 | 0 187 |
| Mean value ($\bar{X}$) | 0.0004$^4$ | 0.126$^4$ | 0.176 | 0.186$^8$ |
| Standard deviation ($\sigma$) | 0.002$^5$ | 0.029$^5$ | 0.015$^2$ | 0.003$^3$ |

TABLE 2

Time required for completing the extraction of oxygen in various shapes of nickel
(Extraction temperature: 2,700–3,000° C.)

| | Powder | Wire | Plate |
|---|---|---|---|
| Oxygen | 20–40 sec | 17–40 sec | 15–20 sec |

Table 3 shows the results of experiments in which powder (20 mesh), wire (1 mm dia. with sample wound thereon) and plate (0.4 mm thick with sample wrapped therein) of nickel were each placed in a graphite crucible together with about 0.1 g. of a standard sample (nitrogen 0.0051%) whose nitrogen content had been determined beforehand by the platinum bath method, in an amount corresponding to ten times the weight of the sample and heat-melted at 2,700° to 3,000° C., the resultant nitrogen gas was extracted and nitrogen contained in the sample was quantitatively determined according to a thermal conductivity method. Results obtained in the absence of nickel are also shown in Table 3.

Table 4 shows the results of measuring the time required for completing the extraction of nitrogen gas in melt-extraction.

TABLE 3

Results of nitrogen analysis in various shapes of nickel
(Extraction temperature: 2,700–3,000° C.)

| Number of times of analysis | Nickel Component | | | |
|---|---|---|---|---|
| | Not Added N | Powder (20 mesh) N | Wire (1 m/mdi) N | Plate (0.4 m/mt) N |
| 1 | 0.0001 | 0.0036 | 0.0044 | 0.0051 |
| 2 | 0.0003 | 0.0025 | 0.0051 | 0.0049 |
| 3 | 0.0002 | 0.0016 | 0.0039 | 0.0052 |
| 4 | 0.0001 | 0.0031 | 0.0049 | 0.0046 |
| 5 | 0.0002 | 0.0027 | 0.0031 | 0.0050 |
| Mean value ($\bar{X}$) | 0.0001$^8$ | 0.0027 | 0.0042$^8$ | 0.0049$^6$ |
| Standard deviation ($\sigma$) | 0.0000$^8$ | 0.0007$^5$ | 0.0008$^1$ | 0.0002$^3$ |

TABLE 4

Time required for completing the extraction of nitrogen in various shapes of nickel
(Extraction temperature: 2,700–3,000° C.)

| | Powder | Wire | Plate |
|---|---|---|---|
| Nitrogen | 20–40 sec | 20–40 sec | 20–25 sec |

As is apparent from the above results, although the results obtained in the absence of nickel (namely, sample alone) are out of the question, the oxygen contents obtained using a powdered nickel are far lower than the standard value and exhibit a fairly large scattering of values, while the oxygen contents obtained using a linear nickel are closer to the standard value and exhibit less scattering of values than those obtained using a powdered nickel, but are still not fully satisfactory.

Also as to the extraction time, it is seen that powdered and linear shapes of nickel require long times and are unstable, while the results obtained using a plate-shaped nickel, as compared with powdered and linear ones, indicate a very high accuracy, an extremely small scattering of values, a short extraction time and a high stability.

Figure 1B:
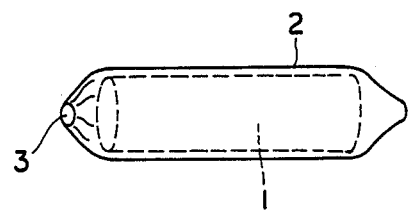

Thus, in melting nickel together with a sample, its plate-like shape integral with the sample wrapped therein is considered to be most preferable for rapid formation of an appropriate melting bath and for promoting the extraction of CO gas. In enclosing the sample in such nickel plate, if the sample is sealed completely, there may occur incorporation of air, so a semi-sealed state having an appropriate vent hole is rather desirable. More particularly, it is recommended to use such a pipe-like capsule as shown in FIG. 1 also in consideration of easiness of the analyzing work. In fabricating this pipe-like capsule, (a) a rod-like sample 1 is inserted into a nickel pipe 2 which has been fabricated in conformity with the diameter and length of the sample 1 and (b) both are rendered integral by caulking both ends of the pipe. The caulking is performed so as to leave a venting hole 3 in a pipe end without sealing the pipe end completely, as shown in the same figure.

The use of such a capsule type is advantageous in that not only the preparation and handling of sample are easy and a high working efficiency is attained, but also the sample-nickel ratio can be adjusted to a desired value by suitably changing the length ($l_1$) of the sample 1 or the length ($l_2$) of the nickel pipe.

Figure 2:
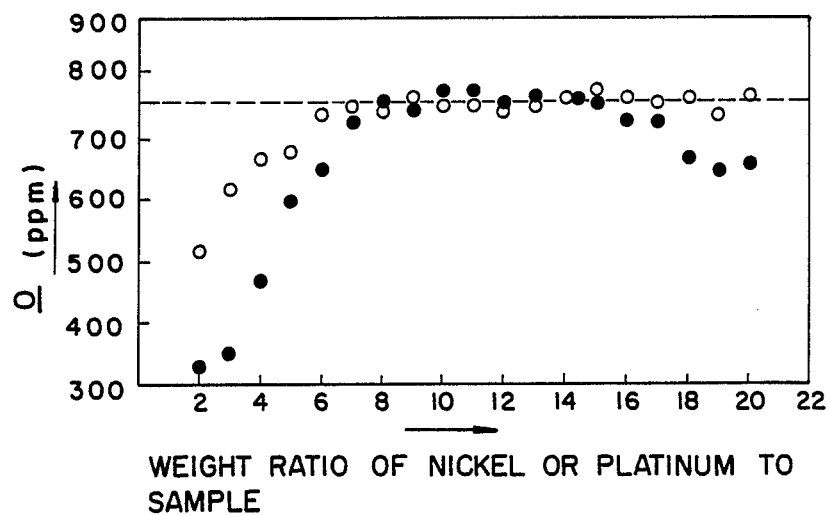
FIG. 2 shows oxygen analysis values with varying nickel to titanium sample weight ratio and also shows oxygen analysis values with varying platinum to the same sample weight ratio.

In connection with the nickel to sample ratio, FIG. 2 shows results (● mark) of oxygen analysis on the sample in which, utilizing the characteristics of the above capsule, 0.1 g. of the sample was inserted into nickel pipes of various lengths to change the nickel to sample weight ratio, and results (o mark) obtained using the platinum bath method in which the platinum to sample weight ratio was changed in the same manner. A standard value of oxygen content of the sample is 760 ppm (as indicated by broken line in FIG. 2), and the melt-extraction temperature was 2,700°–3,000° C.

Figure 3:
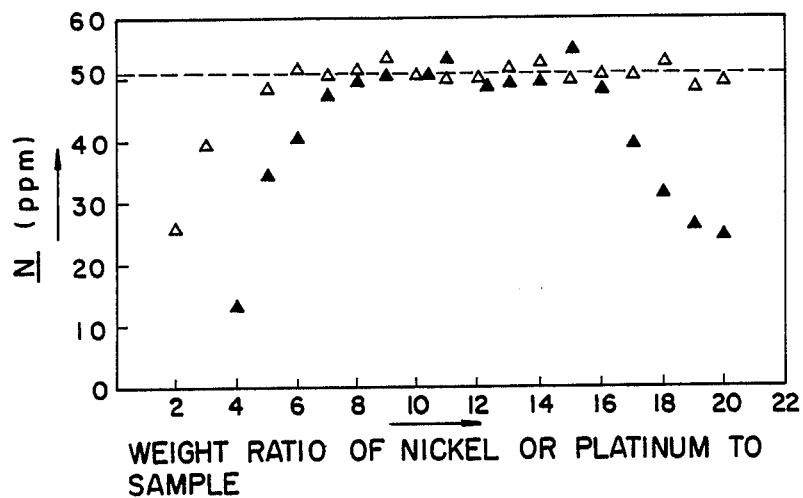
FIG. 3 shows nitrogen analysis values with varying sample weight ratio and also shows nitrogen analysis values with varying platinum to the same sample weight ratio.

Likewise, as to the nickel to sample ratio, FIG. 3 shows results (▲ mark) of nitrogen analysis on the sample in which, utilizing the characteristics of the above capsule, 0.1 g. of the sample was inserted into nickel pipes of various lengths to change the nickel to sample weight ratio, and results (Δ mark) obtained using the platinum bath method in which the platinum to sample weight ratio was changed in the same manner. A standard value of nitrogen content of the sample is 51 ppm (as indicated by broken line in FIG. 3), and the melt-extraction temperature was 2,700°–3,000° C.

From the above figures it is seen that in the presence of nickel, if the nickel to sample weight ratio is too small or too large, an extremely low accuracy results in comparison with the platinum bath method. Therefore, in order to ensure an analytical accuracy comparable to that in the platinum bath method, it is necessary to maintain the proportion of nickel in an appropriate range. Particularly, it is clearly recognized that if the nickel to sample weight ratio is lower than 7 or higher than 17 (16 for nitrogen analysis), the value of oxygen or nitrogen obtained tends to be fairly lower than the standard value. And thus such nickel to sample weight ratio is considered to be unpractical. It is therefore essential in the present invention that the above weight ratio be in the range of 7 to 17 (7 to 16 for nitrogen analysis), that is, the proportion of nickel to be adjusted in the range of 7 to 17 (7 to 16 for nitrogen analysis times, preferably 8 to 15 (8 to 16 in nitrogen analysis) times, the weight of the sample.

Table 5 shows results of oxygen analysis obtained according to the method of the present invention with respect to samples containing oxygen of various values which satisfy the condition on the proportion of nickel defined above, and results of oxygen analysis obtained according to the platinum bath method with respect to those samples. Both results are closely coincident with each other, proving that the method of the present invention has an analytical accuracy equal to that of the platinum bath method.

Table 6 shows analysis and comparison of blank values of nickel and platinum, from which it is seen that the values of oxygen in nickel are equal to or smaller than those in platinum;, thus proving a very small influence of blanks.

TABLE 5

Results of oxygen analysis according to the method of the present invention (unit %)

| Sample Name | | | |
|---|---|---|---|
| | No. 1(Round Bar) | No. 2(Plate) | Titanium Institute Standard No. 2 |
| | Element for Analysis | | |
| Number of times of analysis (Nickel Bath Method) | O | O | O |
| | Platinum Bath Method | | |
| | X; 0.076 | X; 0.187 | X; 0.110 |
| | σ; 0.0024 | σ; 0.0025 | σ; 0.0025 |
| 1 | 0.074 | 0.185 | 0.110 |
| 2 | 0.075 | 0.188 | 0.112 |
| 3 | 0.079 | 0.183 | 0.112 |
| 4 | 0.075 | 0.187 | 0.115 |
| 5 | 0.077 | 0.190 | 0.113 |
| 6 | 0.072 | 0.186 | 0.114 |
| 7 | 0.078 | 0.189 | 0.115 |
| 8 | 0.076 | 0.118 | 0.113 |
| 9 | 0.073 | 0.184 | 0.110 |
| 10 | 0.075 | 0.184 | 0.109 |
| Mean value ($\overline{X}$) | $0.075^4$ | $0.186^4$ | $0.112^3$ |
| Standard deviation (σ) | $0.002^2$ | $0.0023^7$ | $0.002^1$ |

TABLE 6

| | Blank values of nickel and platinum | |
|---|---|---|
| Number of times of analysis | Nickel O | Platinum O |
| 1 | 2.2 | 5.2 |
| 2 | 3.2 | 4.2 |
| 3 | 2.4 | 4.0 |
| 4 | 3.8 | 6.0 |
| 5 | 4.0 | 5.7 |
| 6 | 3.5 | 6.5 |
| 7 | 2.7 | 4.5 |
| 8 | 2.5 | 5.5 |
| 9 | 3.0 | 5.2 |
| 10 | 3.1 | 4.8 |
| Mean value ($\overline{X}$) | $3.0^4$ | $5.1^6$ |
| Standard deviation (σ) | $0.6^0$ | $0.8^0$ |

Table 7 shows results of nitrogen analysis obtained according to the method of the present invention with respect to samples containing nitrogen of various values which satisfy the condition on the proportion of nickel defined above, and results of nitrogen analysis obtained according to the platinum bath method with respect to those samples. Both results are closely coincident with each other, proving that an analytical accuracy equal to that of the platinum bath method can be attained by the method of the present invention.

Table 8 shows analysis and comparison of blank values of nickel and platinum, from which it is seen that the values of nitrogen in nickel are about five times those in platinum but are about 0.5 ppm which is extremely low and negligible in comparison with the value of nitrogen in an actual sample, thus causing no problem in practical use.

TABLE 7

Results of nitrogen analysis according to the method of the present invention

| | Sample Name | | |
|---|---|---|---|
| | No. 1(Round Bar) | No. 2(Plate) | Titanium Institute Standard No. 2 |
| | Element for Analysis | | |
| Number of times of analysis (Nickel Bath Method | N | N | N |
| | Platinum Bath Method | | |
| | X; 0.0018 | X; 0.0051 | X; 0.0042 |
| | σ; 0.0002 | σ; 0.0005 | σ; 0.00035 |
| 1 | 0.0016 | 0.0047 | 0.0043 |
| 2 | 0.0018 | 0.0050 | 0.0043 |
| 3 | 0.0020 | 0.0051 | 0.0044 |
| 4 | 0.0019 | 0.0048 | 0.0040 |
| 5 | 0.0017 | 0.0049 | 0.0045 |
| 6 | 0.0019 | 0.0051 | 0.0045 |
| 7 | 0.0018 | 0.0053 | 0.0046 |
| 8 | 0.0010 | 0.0052 | 0.0041 |
| 9 | 0.0017 | 0.0049 | 0.0041 |
| 10 | 0.0018 | 0.0050 | 0.0043 |
| Mean value (X) | $0.0017^8$ | $0.0050^0$ | $0.0043^1$ |
| Standard deviation (σ) | $0.0001^3$ | $0.0001^8$ | $0.0002^0$ |

TABLE 8

Blank values of nickel and platinum

| Number of times of analysis | Nickel N | Platinum N |
|---|---|---|
| 1 | 0.7 | 0.1 |
| 2 | 0.4 | 0 |
| 3 | 0.4 | 0.2 |
| 4 | 0.3 | 0.1 |
| 5 | 0.8 | 0 |
| 6 | 0.5 | 0.1 |
| 7 | 0.6 | 0 |
| 8 | 0.7 | 0 |
| 9 | 0.4 | 0.1 |
| 10 | 0.3 | 0.2 |
| Mean value (X) | $0.5^1$ | $0.0^8$ |
| Standard deviation (σ) | $0.1^8$ | $0.0^8$ |

In this melt-extraction performed in the presence of nickel according to the present invention, the form and proportion of the nickel are important as previously noted. In addition, as to the melt-extraction temperature, ample care should be exercised. Taking into account the accuracy and rapidness of analysis, including a rapid formation of a molten bath of nickel and titanium and an efficient promotion of the extraction of CO gas or nitrogen gas, it is advantageous to set the melt-extraction temperature at a level not lower than 2,000° C., especially in the range of 2,400° to 3,000° C., in the oxygen analysis, and in the nitrogen analysis the temperature should be set in the range of 2,700° to 3,000° C.

Figure 4:
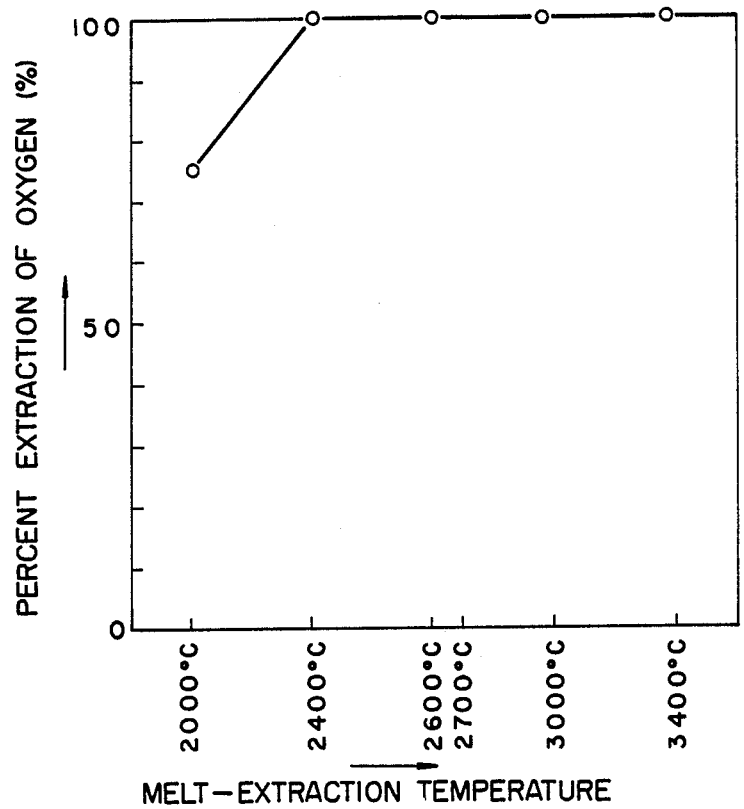
FIG. 4 shows a relation between melt-extraction temperature and percent extraction of oxygen.

In this connection, FIG. 4 shows a relation between melt-extraction temperature and percent extraction of oxygen obtained in oxygen analysis experiments performed by inserting a standard titanium sample with an oxygen content of 1,870 ppm into a nickel pipe followed by melt-extraction at various temperatures and subsequent analysis of oxygen. From this figure it is seen that even at 2,000° C. there is obtained a relatively high percent extraction of 75%, and a 100% extraction is attained at 2,400° C., thus proving the possibility of practical application. However, at temperatures exceeding 3,000° C., the erosion of the crucible becomes severe, making extraction unstable, therefore not desirable in practical use.

FIG. 5 shows a relation between melt-extraction temperature and percent extraction of nitrogen obtained in nitrogen analysis experiments performed by inserting a standard titanium sample with a nitrogen content 51 ppm into a nickel pipe followed by melt-extraction at various temperatures and subsequent analysis of nitrogen. From this figure it is seen that at temperatures not lower than 2,700° C. there are obtained superior results as reflected in 100% extraction although at temperatures not higher than 2,600° C. the percent extraction is fairly low, not more than 20%. However, temperatures exceeding 3,000° C. are not desirable because the crucible erosion become severe, making extraction unstable.

What is claimed is:

1. A method for quantitatively analyzing the nitrogen-content of a titanium group metal or an alloy of a titanium group metal, said method comprising:
   (i) melting a sample of a titanium group metal or an alloy in an inert gas atmosphere in the presence of nickel, said nickel being present in an amount corresponding to 7 to 16 times by weight the weight of the sample whereby nitrogen is extracted therefrom;
   (ii) subjecting extracted nitrogen to quantitative analysis.

2. The method of claim 1, comprising melting the titanium metal or the alloy at a temperature of from 2,700° C. to 3,000° C.

3. The method of claim 1, comprising melting the sample of the titanium group metal or the alloy in presence of nickel, wherein the nickel is present in an amount corresponding to 8 to 16 times by weight the weight of the sample.

4. The method of claim 1, comprising using nickel having a purity of 99% by weight.

5. The method of claim 1, comprising using nickel in powder form.

6. The method of claim 1, comprising using nickel in wire form.

7. The method of claim 1, comprising using nickel in plate form.

* * * * *

UNITED STATES PATENT AND TRADEMARK OFFICE
CERTIFICATE OF CORRECTION

PATENT NO.  : 4,746,617
DATED       : May 24, 1988
INVENTOR(S) : Masayoshi OKAMURA, et al.

It is certified that error appears in the above-identified patent and that said Letters Patent is hereby corrected as shown below:

- The following Foreign Application Priority Data should be indicated on the Title page:

-- Jun. 1, 1984  [JP]  Japan .............. 59-113762
     Jun. 1, 1984  [JP]  Japan .............. 59-113763 --

On the title page "4 Drawing Sheets" should read

-- 3 Drawing sheets --.

Signed and Sealed this

Eighth Day of November, 1988

Attest:

DONALD J. QUIGG

Attesting Officer

Commissioner of Patents and Trademarks